(12) United States Patent
Archipiano et al.

(10) Patent No.: US 8,969,658 B2
(45) Date of Patent: Mar. 3, 2015

(54) METHOD FOR PRODUCING HAPLOID, DOUBLED HAPLOID AND/OR DIHAPLOID PLANTS BY GYNOGENESIS

(75) Inventors: Muriel Archipiano, Beaumont de Lamagne (FR); Daniele Hosemans, Angers (FR); Eric Lionneton, Bouchemaine (FR); Agnes Vermuelen, Cheminas (FR)

(73) Assignee: HM. Clause, Portes les Valence (FR)

( * ) Notice: Subject to any disclaimer, the term of this patent is extended or adjusted under 35 U.S.C. 154(b) by 1078 days.

(21) Appl. No.: 13/055,210

(22) PCT Filed: Jul. 21, 2009

(86) PCT No.: PCT/EP2009/059376
§ 371 (c)(1),
(2), (4) Date: May 16, 2011

(87) PCT Pub. No.: WO2010/010096
PCT Pub. Date: Jan. 28, 2010

(65) Prior Publication Data
US 2011/0214201 A1    Sep. 1, 2011

(30) Foreign Application Priority Data
Jul. 21, 2008  (FR) ...................................... 08 54952

(51) Int. Cl.
*A01H 1/08* (2006.01)
*A01H 1/04* (2006.01)
*A01H 4/00* (2006.01)
*C12Q 1/68* (2006.01)

(52) U.S. Cl.
CPC .. *A01H 4/00* (2013.01); *A01H 1/08* (2013.01); *C12Q 1/6827* (2013.01); *C12Q 2600/13* (2013.01)
USPC ......... 800/299; 800/267; 800/310; 435/430.1

(58) Field of Classification Search
None
See application file for complete search history.

(56) References Cited

FOREIGN PATENT DOCUMENTS
WO    2004/072259    8/2004

OTHER PUBLICATIONS

Caglar et al. Proc. First Int. Symp. on Cucurbita. Acta Horticulturae 492: 317-322 (1999).*
Chiba et al. Breeding Science 53: 21-27 (2003).*
Database EMBL [Online], "Cucurbita pepo omega-6 fatty acid desaturase (FAD2) mRNA, complete cds.", XP002550301, (Accession No. AY525163) (Feb. 2004).
Froelicher et al., Plant Cell Reports, 26(7):937-944 (2007), XP002519882.
Gonzalo et al., Theoretical and Applied Genetics, 110(5):802-811 (2005), XP002519884.
International Search Report in PCT/EP09/59376, dated Dec. 22, 2009.
Kurtar et al., Euphytica, 127(3):335-344 (2002), XP002558905.
Sauton et al., Argonomie, 7(2):141-147 (1987), XP008103758.
Shalaby, Scientia Horticulturae, 115(1):1-6 (2007), XP022340589.
Tang et al., Plant Cell Tissue and Organ Culture, 84(2):233-237 (2006), XP002519883.

* cited by examiner

*Primary Examiner* — David T Fox
(74) *Attorney, Agent, or Firm* — McAndrews, Held & Malloy Ltd.

(57) ABSTRACT

The invention relates to a method for producing haploid H, doubled haploid HD and/or dihaploid DH plants, the HD and DH being homozygous or essentially homozygous, this method being a method such as those which come under the technique of gynogenesis induced by irradiated pollen. This method comprises a step of irradiating the reproductive material of the male parent at a dose of between 160 and 190 gamma ray and/or a step of selecting the haploid H and/or DH plants by using one or more molecular marker(s). The invention also relates to a method for producing homozygous haploid, doubled haploid and/or dihaploid plants, comprising a step of determining the appropriate irradiation dose(s) for increasing the yields of said plants according to multiple given factors such as the plant species, the genotypes of the male parent and of the female parent, the climatic and weather conditions, the time at which the fruits are harvested, the level of growth of the embryos collected with a view to the culturing thereof, the level of development of the embryos placed in culture. Moreover, the invention concerns the molecular marker(s) used in the selection step and also the haploid embryos and the dihaploid embryos obtained by means of the method of the invention, and the progeny and the seeds of the plants obtained by means of the method of the invention.

8 Claims, No Drawings

METHOD FOR PRODUCING HAPLOID, DOUBLED HAPLOID AND/OR DIHAPLOID PLANTS BY GYNOGENESIS

The present application is filed pursuant to 35 U.S.C. 371 as a U.S. National Phase application of International Patent Application No. PCT/EP09/59376, which was filed Jul. 21, 2009, claiming the benefit of priority to French Patent Application No. 0854952, which was filed on Jul. 21, 2008. The entire text of the aforementioned applications is incorporated herein by reference in its entirety.

The field of the invention is that of plant selection or improvement, namely the production of plants both in the form of embryos and at any other stage, notably from the plantlet to the adult plant.

More precisely, plant selection or improvement according to the present invention signifies obtaining a homozygous or essentially homozygous haploid or diploid plant having progeny that is stable in terms of its phenotypic and/or genotypic characters. In other words, for such a plant this leads to fixation of its genome with a reduced number of generations (for example one or two).

Even more precisely, the present invention relates to a novel method for producing plants (e.g. embryos, plantlets, adult plants) that are Haploid (H), Doubled Haploid (DH) and/or DiHaploid (DiH), homozygous or essentially homozygous, this method being a method such as those which come under the technique of gynogenesis advantageously associated with irradiation of pollen. The plants in question are for example zucchini.

The systems for creating varieties, namely the creation of novel plants to meet the specific needs of farmers and producers, have accelerated since the beginning of the 20th century. One of the most radical changes was the development of hybrids, also called F1 hybrids commercially, initially in maize, and utilization of the phenomenon of heterosis, which corresponds to increase in the capacities or vigor of a hybrid for a number of characters (vigor, yield, resistance to diseases and lodging resistance, precocity) above the average of the two parents or above the best of the two parents. Another change relates to the use of in vitro plant culture techniques based on their totipotency.

The creation of F1 hybrid plants, notably making it possible to combine, in the F1 hybrid plant, the dominant characters of its parents, was quickly extended from maize to other species such as tomato, peppers, eggplants. In fact, in addition to the hybrid vigor present in certain species, obtaining F1 hybrids also makes it possible to improve the plant's capacities for homeostasis (stability of the plant and of expression of its characters in different environments), and the possibility of accumulating genes of interest. However, the creation of F1 hybrid plants involves the creation of relatively homozygous parental lines. Once crossed, these parental lines make it possible to obtain the F1 hybrid. As long as the genetic purity of the parental lines is maintained, the F1 hybrids can be obtained repeatedly.

This quest for homozygosity of the parental lines was not developed solely for obtaining F1 hybrid plants. Similarly, during development of new plants marketed in the form of population varieties (lettuce, haricot, corn salad, etc.), the creation of relatively homozygous cultivars (or varieties) has become imperative. The requirements of product homogeneity for farmers and for marketing (criteria of homogeneity and stability of new cultivars included in the list), as well as mechanization and the increasing precision of techniques for culture and production, lead to the need for plants that are more and more homogeneous in expression of their characters.

The plant breeder traditionally gets closer to the level of required homozygosity by self-fertilizing the most promising plants over several generations, selecting those that have the required characters, thus progressively homogenizing the genome of the plants from one generation to the next.

The new zucchini plants developed by plant breeders are either autogamous cultivars, or F1 hybrids. In both cases, achieving homogeneity of the cultivar and/or of the parental lines of the F1 hybrid is one of the goals of the selection program.

It will be recalled that to initiate the sexual cycle of plants, a process of reduction of the number of chromosomes (meiosis) is necessary to give rise to gametes having a haploid chromosome number (n). In flowering plants, sexual reproduction involves double fertilization. The pollen grain produces two male gamete nuclei (n) or reproductive nuclei. A male nucleus fuses with an ovule (n) to form a zygote (2n) which produces the embryo by restoring the number of somatic chromosomes (2n). Another male nucleus (n) combines with the haploid polar nuclei of the embryo sac, to form a triploid cell (3n). In certain cases, formation of the zygote does not occur, but cell divisions of the ovule are nevertheless initiated, resulting in a haploid embryo capable of giving rise to a plantlet whose haploid genome originates entirely from the female plant (Sarkar and Coe, Genetics, 1966, Vol. 54, 453-464). Haploid plants occur in small numbers in nature and are sterile.

The discovery, at the beginning of the 1920s, of viable haploid plants and of the possibility of doubling their chromosome stock was the stimulus for much research. In fact, these haploid plants are interesting not only in the field of genetics but also for plant improvement because, after chromosome doubling (whether or not spontaneous), the genetic information is identical on the two chromosomes of each pair. Accordingly, the genetic information is fixed and the doubled haploids can speed up the selection processes.

In 1964, Guha and Maheshwari (Guha and Maheshwari, *Nature*, 1964, 204, 497) discovered that plants can be regenerated from haploid cells during culture of pollen grains.

Since then, numerous studies have investigated the production of haploid plants of various species, using techniques of in vitro culture of gametophytes. The two main techniques for production of embryos and haploid plants (haploidization) by in vitro culture of gametophytes are androgenesis and gynogenesis.

In androgenesis, immature male gametophytes are cultured on a synthetic medium in order to obtain haploid embryos, which then develop into complete plants. The results vary with the genotype, but also with the protocols used.

In gynogenesis, it is the mature female gametophytes (ovaries or ovules) that are cultured.

The two techniques can be used on the same species, knowing that one of them is more advantageous for certain species, whereas the other technique is more suitable for other species.

Some authors also mention the production of embryos and of haploid plants by the use of chemical or physical agents. The principle of this technique is to bring about the development of the unfertilized ovule on the plant (in situ). Although trials with thermal shock, X-rays or chemicals only gave mediocre results, the use of irradiated pollen gave, in certain species such as the melon, results that are not directly applicable to other species.

The majority of the plants induced by these techniques are haploid plants, but other plants with variable levels of ploidy can be obtained. Although aneuploids or tetraploids may only be of minor interest in plant improvement programs, spontaneous diploids (dihaploids DiH) are for their part very sought-after, since the spontaneous doubling of their chromosome stock during the first phases of culture in vitro renders them fertile. These homozygous plants can be used directly by plant breeders, which represents an enormous advantage on several levels (time, space, cost, etc.).

The Haploid plants (H) that are obtained by these various techniques and that have not spontaneously doubled their chromosome stock must then undergo an additional stage to render them diploid (2n) or Doubled Haploids (DH). This can be done by means of various chemicals such as colchicine (an alkaloid that permits doubling of a chromosome stock).

The doubled haploids DH as well as the dihaploids DiH (resulting from spontaneous diploidization) are homozygous individuals, which can be used notably directly as homogeneous cultivars (population varieties) or as parental lines of hybrid varieties. In fact, these DH and DiH plants carry, in doubled form, the genetic information of a single set (n) of chromosomes, that of the female gamete from which they were originally derived.

Thus, these techniques for creation of plants in vitro not only save time, but also lead to better genetic homogeneity: the genome is stabilized (homozygous) in a single generation instead of approaching genomic homozygosity after multiple generations of self-fertilization. They also make it possible to improve the selection program since they emphasize the recessive characteristics of the plant thus created. The use of doubled haploids DH and dihaploids DiH is therefore a very interesting tool. Its use has been widely adopted for certain species: androgenesis is used for plants of the genus *Brassica* (Keller et al., in K. Giles, S. Sen (eds.), Plant Cell Culture in Crop Improvement, 1984, 169-183. Plenum Pub. Corp., New York), gynogenesis for cucumber (European patent EP 0374755) and sugar beet (Hosemans and Bossoutrot, Z. Pflanzenzuecht, 1983, 91, 74-77), irradiated pollen for melon (Sauton and Dumas de Vaulx, *Agronomie* 7, 1987, 7 (2), 141-148).

In consequence, plants for the development of which techniques of haploidization in vitro were used are now available commercially in various species and are included in the official list.

However, despite these few commercial varieties, the yields of the various methods of haploidization are still too dependent on multiple factors that are unknown or imperfectly controlled (genotype, culture of the mother plants, conditions in which haploidization is performed, etc.) and are sometimes still too low, in many species, to be integrated routinely in the existing methods of selection.

With regard to zucchini *Cucurbita pepo*, to date only a few fragmentary results are known and none indicates how to produce sufficient haploid embryos H (which then give the doubled haploids DH), or dihaploid embryos DiH for supplying a plant improvement program.

The first mention of the culture in vitro of unfertilized ovules of *Cucurbita pepo* is reported by Dumas de Vaux and Chambonnet in 1986 (Dumas and Chambonnet, *Genetic Manipulation in Plant Breeding*, 1986, 285). The ovules are extracted from the ovaries one or two days before flowering or that very morning. In the first two cases, the flowers are not pollinated, in the third, they are pollinated but not fertilized. The ovules are placed in Petri dishes on a medium containing macro- and micronutrients, as well as vitamins, 2,4-dichlorophenoxyacetic acid (2,4-D) and kinetin. The authors obtain their best yield, i.e. 4.3 embryos per 100 ovules cultivated, when the ovaries are taken one day before flowering. However, they encounter difficulties in obtaining plants that develop normally. The origin of the plants is analyzed during a subsequent stage of self-pollination of the fertile diploid plants and phenotypic examination of the progeny.

More recently, still with regard to zucchini *Cucurbita pepo*, Shalaby (Shalaby, *Scientia Horticulturae*, 2007, 115, 1-6) analyzed the influence of the genotype, the position of the female flowers on the stem, the temperature and the sucrose concentration during gynogenesis. The regenerated haploid plants are treated with colchicine in order to obtain doubled haploids. The authors conclude that the genotype used has a considerable influence on the possibilities for routine use of this technique. Thus, the genotype Yellow Bik does not produce an embryo by gynogenesis whereas it responds to androgenesis.

The conclusion of this article regarding the influence of the genotype clearly states that the techniques of androgenesis and of gynogenesis are not yet satisfactory for extensive, routine use in a program for improvement of zucchini *Cucurbita pepo*.

It has been proposed to irradiate pollen in a method of induced gynogenesis for obtaining haploid plants H, and/or dihaploid plants DiH, the haploid plants H then giving doubled haploid plants DH. Irradiation of the pollen grain causes it to lose its fertilizing capacity (the DNA of the gametes is damaged by the radiation) but it conserves its germinating capacity, and can thus induce division of the oosphere and its development to an embryo.

This technique of gynogenesis with irradiation of pollen is used notably for the melon (*Cucumis melo*) (Sauton, Cinquantenaire de la Culture in vitro, 24-25 Oct. 1989) where the major proportion of the genotypes is capable of producing haploid or dihaploid embryos and/or plants.

Irradiation of pollen is also employed in the technique of gynogenesis employed for zucchini *Cucurbita pepo* and reported by Kurtar et al. (Kurtar et al., *Euphytica*, 2002, 127, 335-344). Kurtar et al. investigated the influence of irradiation dose and genotypes on the production of haploid embryos. These authors obtain haploid embryos and plants without having been able to optimize the irradiation dose and having established that the production of embryos is strongly influenced by the level of irradiation, by the development of the embryos placed in culture and by the genotypes. Thus, in contrast to what occurs with the melon, the technical conditions of production of haploid embryos of zucchini *Cucurbita pepo* cannot yet be generalized.

This multifactorial variability constitutes a first notable drawback of the known methods of gynogenesis, with or without irradiation of pollen.

A second drawback of said methods relates to analyses of the state of ploidy and of the state of homozygosity of the plants obtained (embryos/plantlets/adult plants). In fact, the plants can be haploid or dihaploid, but they can have various levels of ploidy, and can notably be haploid-diploid chimeras, tetraploids or aneuploids (Dumas de Vaux and Chambonnet in 1986).

Contradicting the principle of gynogenesis, irradiation of pollen can give rise to fertilization of the ovule by the DNA of the pollen grain, principally by fragments of DNA. This can arise because the radiation has not degraded the DNA sufficiently to prevent partial fertilization, resulting in the formation of a chimeric embryo (without wishing to be limited by any theory, the present inventors are thinking of recombinations between the DNA of the ovule and DNA fragments of the pollen grain). When the radiation degrades the DNA sufficiently, the pollen grain should lose its fertilizing capacity and only conserve its germinating capacity. However, it was found that in certain cases, during extension of the pollen tube, fragments of male DNA may come in contact with the ovule and, during pseudofertilization, recombine with the female DNA, thus giving haploid chimeric plants (when recombination between the DNA of the ovule and the fragments of the DNA of the irradiated pollen grain is followed by loss of the excess DNA during subsequent cell divisions) or plants with varied ploidy, which can notably be heterozygous for certain genes when they bear one or more supernumerary chromosomes. The haploid chimeric plants are interesting since they only possess a single copy of the genetic information (even if a tiny part of the genome comes from the male gamete) and a doubling of their chromosome stock, similarly to the haploids, produces homozygous or essentially homozygous plants.

Diploid heterozygous plants resulting from "classical" fertilization can also be produced, for example in the case of insufficient irradiation.

Moreover, in the Cucurbitaceae, it was found that certain plants obtained by these various methods of culture in vitro can be diploid but heterozygous as they do not undergo gametic reduction during formation of the female gametes (Veilleux, *Plant Breeding Reviews,* 1985, 3, 253-288). They thus bear all of the genetic information of the original plant and therefore do not have the required interesting characteristics that are typical of haploid, DH and/or DiH plants.

The known methods for determining the levels of ploidy make it possible to differentiate haploid plants n from diploid plants 2n. However, existing methods for finer determination of the level of ploidy (chimerism, missing or supernumerary chromosomes or fragments of chromosomes) are still very costly in terms of equipment and time. Thus, a simple, quick and economical method would be required for distinguishing between haploid plants and chimeric plants resulting from pseudofertilization. Moreover, at present, there is no satisfactory possibility for differentiating heterozygous diploid 2n plants resulting from fertilization, heterozygous diploid 2n plants resulting from gametic nonreduction and homozygous dihaploid DiH diploid 2n plants resulting from spontaneous doubling.

The haploids H (chimeric or nonchimeric) and the various diploids can be identified by cytological analysis, notably by counting the chromosomes in preparations of root cells of plants using an optical microscope. Cytological analysis is difficult to implement in a program for creation of varieties, where speed and accuracy are required. However, this does not solve the problem of identification of the haploids relative to the nonhaploid chimeras resulting from pseudofertilization.

Diploid plants 2n are selected at present by phenotypic analysis of the progeny of the regenerated plant; self-pollination of a homozygous plant should give homogeneous progeny that remains stable through successive generations of self-fertilization. If it does not and if segregation of characters is observed, this means that the regenerated plant was not homozygous, but heterozygous. Thus, to date it has only been possible to identify dihaploids DiH by morphological selection and/or the use of recessive markers (for example, liguleless, glossy, etc.) present in the genome of the female parent. The use of these recessive markers has the drawback that it requires, prior to induction of gynogenesis, their insertion into the genome of the line that is to be used as the female parent, if it does not have them already. Color markers can be used in the selection of haploid or dihaploid embryos and plants (Chase and Nanda, Maize Gen Coop, 1965, Newsletter, 39, 59-60; Coe and Sarkar, J of Heredity, 1964, Vol. 55, 231-233). However, expression of these markers is influenced by the genotype of the female parent or even by the general process of maturation of the embryo and this can lead to incorrect evaluation of the origin of the individuals obtained.

Phenotypic analysis of the progeny takes a long time, since it is necessary to wait for flowering, obtain the seeds and observe the progeny from each seed in order to verify its homogeneity.

The causes of the lack of satisfactory results in these various known methods of haploidization partly reside in the existing limits of the in vitro culture techniques, namely the great genotypic specificity of response to culture in vitro, the low percentages of differentiation to give rise to embryos, the considerable loss of these embryos when we wish to take them to complete organogenesis.

Therefore, to date, there is no satisfactory technique for producing, reproducibly, sufficient haploid H, doubled haploid DH and/or dihaploid DiH plants (e.g. embryos/plantlets/ adult plants), to supply a selection program, notably for zucchini. *Cucurbita* and in particular *Cucurbita pepo* in fact form part of these species where the effort expended is very considerable for overcoming these various problems.

In this context, one of the aims of the present invention is to supply a powerful method for improving the production of haploid H, doubled haploid DH and/or dihaploid DiH plants, by gynogenesis induced by an irradiated male gametophyte (for example irradiated pollen).

Another aim of the present invention is to supply a novel improved method of plant selection or improvement, i.e. for obtaining a haploid or diploid, homozygous or essentially homozygous plant having progeny that is stable with respect to its phenotypic and/or genotypic characters, or in other words a plant for which stabilization of the genome is acquired with a reduced number of generations (for example one or two).

Another aim of the present invention is to supply a method for producing haploid, doubled haploid and/or dihaploid plants, by induced gynogenesis with irradiation of the male gametophytes (pollen), overcoming the drawbacks of the prior art and satisfying at least one of the following specifications:

Optimization of the irradiation dose;
Being able at least partly to avoid the influence of the level of development of the embryos placed in culture and/or of the genotypes and/or of the climatic conditions and/or of the time of harvesting of the fruits, of the level of growth of the embryos collected with a view to culturing them, among others (multifactorial variability);
Generalization of the method to a maximum number of species and genera, in particular to the majority of the zucchini *Cucurbita pepo;*
Permitting efficient and reliable analysis of the state of ploidy and of the origin of the plants produced;
Permitting good identification of the plants obtained.

Another aim of the present invention is to supply a method for producing haploid plants (then giving doubled haploid plants) and/or dihaploid plants, by gynogenesis induced by irradiated pollen, said method making it possible to reduce both the culture time and space necessary for the creation and selection of varieties, owing to a stage of selection of haploid and/or dihaploid plants, from all of the plants with varied ploidy produced.

Another aim of the present invention is to supply a method that makes it possible, upstream of a method for producing haploid and/or dihaploid plants by gynogenesis with irradiation of the reproductive material from the male parent, to determine the suitable irradiation dose for increasing the yields in production of said plants as a function of multiple given factors and preferably selected from the plant species, the genotypes of the male parent and of the female parent, the climatic and physiological conditions of these plants, the time of harvesting of the fruits, the conditions for growth of the immature embryos collected with a view to culture thereof.

Another aim of the invention is to supply at least one of the following objects:
Molecular marker(s);
Embryos;
Plants regenerated from the embryos;
Progeny of the plants;
Seeds from the plants;
usable in or obtained by a method for producing haploid, doubled haploid and/or diplohaploid plants, by gynogenesis induced by irradiated pollen, said method being of the type envisaged in the above aims.

Another aim of the invention is to supply a powerful method of analysis of the origin of plants, notably of plants produced by a method for producing haploid plants (then giving doubled haploid plants) and/or dihaploid plants, by gynogenesis induced by irradiated pollen, said method being of the type envisaged in the above aims, and making it possible to determine whether the plants contain genetic material from the male parent.

Another aim of the invention is to supply a powerful method for the identification of plants, notably of plants produced by a method for producing haploid plants (then giving doubled haploid plants) and/or dihaploid plants, by gynogenesis induced by irradiated pollen, said method being of the type envisaged in the above aims and making it possible to determine whether the plants are homozygous or heterozygous.

At least one of the above aims, among others, is achieved by the present invention, which relates firstly to a novel method for producing haploid H, doubled haploid DH and/or dihaploid DiH plants, the DH and DiH being homozygous or essentially homozygous, said method being a method such as those which come under the technique of gynogenesis induced by irradiated pollen, characterized in that it comprises:
  a stage of irradiation of the reproductive material from the male parent at a dose between 160 and 190 Gamma Ray, preferably between 165 and 185 Gamma Ray (GY),
  or a stage of selection of haploid plants H, or DiH, or H and DiH by the use of a molecular marker,
  or a stage of irradiation of reproductive plant material from the male parent at a dose between 160 and 190 Gamma Ray, preferably between 165 and 185 Gamma Ray (Gy) and a stage of selection of the haploid plants H, or DiH, or H and DiH by the use of a molecular marker.

It should be noted that in the present application, classically the indefinite article "a" must be regarded as a generic plural (meaning "at least one" or "one or more"), except when the context shows otherwise (1 or "a single"). Thus, for example, when it is stated above that a stage of irradiation is added, this means the addition of one or more stages of irradiation. The same applies to the stage of selection of the plants, which can be done by several stages of selection, for the use of one or more molecular markers.

The method according to the present invention opens up a novel route for obtaining plants (*lato sensu*) that are haploid H, doubled haploid DH and/or dihaploid DiH. This novel route supplies improvements in terms of:
  extending the range of plants covered by this technique of gynogenesis with irradiation of the male gametophytes (pollen);
  reduction of the multifactorial variability that was previously characteristic of this technique;
  analysis of the state of ploidy of the plants produced;
  identification of the origin of the plants obtained;
  reduction of the culture time and space necessary for the creation and selection of varieties.

Moreover, this method has proved entirely appropriate for zucchini plants.

Taking into account the factorial variability of gynogenesis induced by irradiation of pollen, all the advances in terms of optimization are welcome. Thus, according to another of its aspects, the invention relates to a method for producing haploid H, doubled haploid DH and/or dihaploid DiH plants, DH and DiH being homozygous or essentially homozygous, by gynogenesis induced by irradiation of the reproductive material from the male parent, characterized in that it comprises a prior stage of determination of the suitable irradiation dose or doses for increasing the yields in production of said plants as a function of multiple given factors and preferably selected from the plant species, the genotypes of the male parent and of the female parent, the climatic and physiological conditions, the time of harvesting of the fruits, and the level of growth of the embryos collected with a view to culture thereof.

The invention also relates to a method for producing haploid H, doubled haploid DH and/or dihaploid DiH plants, DH and DiH being homozygous or essentially homozygous, by gynogenesis induced by irradiated pollen, characterized in that it comprises the use of a molecular marker for identifying the plants that are free from genetic material from the male parent whose pollen was irradiated or which possess an insufficient amount thereof to cause, in the progeny of said plants, a disjunction of a phenotypic and/or genotypic character, as well as for determining their state of homozygosity.

According to yet another of its aspects, the invention relates to a molecular marker that can be used in the method according to the invention, said marker being selected, for example, from the microsatellite markers (SSR), defined by the pairs of primers of the appended nucleotide sequences SEQ ID No. 1 to 16, preferably SEQ ID No. 3 to 14.

According to yet another of its aspects, the invention relates to haploid embryos H, DH and/or DiH of plants, as intermediates of the method according to the invention.

According to yet another of its aspects, the invention relates to the progeny of the plants obtained by the method according to the invention.

According to yet another of its aspects, the invention relates to the seeds of the plants obtained by the method according to the invention.

For better understanding of the invention, some definitions must first be given or recalled, all of which must be regarded as nonlimiting examples.
  Genotype means all of the genetic material carried by an individual and which constitutes its genetic inheritance. A genotypic character may or may not correspond to a phenotypic character, whether it is recessive or dominant.
  The term phenotype denotes all of an individual's morphological or functional characters, which correspond both to the part of the genotype that is expressed and to phenomena determined by the environment.
  Plant means a vegetable at any stage of development, notably: embryo, or any other plantlet stage or adult plant.

Male plant or male parent means a plant used as pollen donor in crossing.

Female plant or female parent means a plant used as pollen receptor, or ovule donor in crossing.

Male reproductive material means the male flower or any part having male haploid gametes, namely the stamen, male gametophytes or pollen grains.

For simplicity, in the present application pollen will mean the male reproductive material that is used.

Female reproductive material means the female flower or any part having female haploid gametes, the ovaries, ovules, female gametophytes (embryo sac) or female reproductive cells (oospheres).

An autogamous plant is one whose method of reproduction is autogamy and whose seeds result from the fertilization of two gametes from the same individual.

Pollination means the supply of a pollen grain from the stamen (male organ) onto the female organs. Pollination gives rise to fertilization, or to pseudofertilization, when the male material used is irradiated.

Fertilization means fusion between a male gamete and a female gamete, giving rise to an embryo.

Pseudofertilization means the induced formation of an embryo without the prior fusion of a male and female gamete. Within the scope of the present invention, the technique of gynogenesis induced by irradiation of pollen permits the formation of an embryo by pseudofertilization. Pseudofertilization can also be a partial fertilization, when DNA fragments from the male gamete fuse with the female gamete.

Self-fertilization means the pollination of an individual by its own pollen; the individuals resulting therefrom are said to be self-fertilized.

Hybrid plant means a plant resulting from crossing two genetically different parents. A first-generation plant from a cross between two genetically distinct homozygous parents, for example two distinct varieties, can be called an F1 hybrid.

Heterosis or hybrid vigor means the phenomenon according to which an F1 hybrid is significantly superior to the better of its parents with respect to one or more characters, and notably with respect to vigor.

Chromosome stock means the number of chromosomes contained in the cell nucleus, or the amount of DNA.

Allele means, according to the present invention, the different versions of a given DNA sequence situated at a given chromosome locus (position on a chromosome).

Homozygous means a cell or an individual that possesses two identical alleles of one and the same gene on a specified locus of the same chromosome pair, for the characteristic supplied by said gene.

Essentially homozygous means the plants according to the invention, provided that the identity of the two alleles is verified for example for at least 80%, preferably 85%, notably 90% and more particularly 95%, of the alleles tested, or provided that after self-fertilization there is no segregation of the characters in the progeny.

By extension, in the present application, essentially homozygous plants are regarded as homozygous plants.

Diploid is an attribute applicable to cells or to plants or parts of plants comprising said cells, which have, in their nucleus, a batch of chromosomes that are similar two by two, called homologs. Diploid cells are usually the result of fertilization of two haploid gametes.

Haploid is an attribute applicable to cells or to plants or parts of plants comprising said cells, of which the chromosomes contained in their nucleus are each only a single copy (n).

Chimeric is an attribute applicable to cells or to plants or parts of plants comprising said cells, which comprise an additional DNA fragment derived from irradiated pollen or of which one of the chromosomes has undergone recombination with DNA from irradiated pollen. These cells can be haploid H, dihaploid DiH (when there is spontaneous doubling of the chromosome stock) or with varied ploidy.

When a plant is a chimera with varied ploidy (notably comprising supernumerary chromosomes or fragments of chromosomes), it is heterozygous for certain alleles.

When a plant results from recombination with a DNA fragment of irradiated male pollen, it is interesting in two cases:
1) If it only possesses a single copy of each of the chromosomes, it is regarded as haploid and can therefore undergo subsequent chromosome doubling to become a homozygous doubled haploid (2n) plant.
2) If it has undergone spontaneous chromosome doubling, it is homozygous dihaploid (2n).

Doubled haploid (DH) is an attribute applicable to cells or to plants or parts of plants comprising said cells, whose chromosome stock was multiplied artificially, most often by chemical treatment and mainly with colchicine.

Dihaploid (DiH) is an attribute applicable to cells or to plants or parts of plants comprising said cells, these cells being haploid initially, and whose chromosome stock has doubled spontaneously. This doubling of the chromosome stock makes it possible to obtain a cell, plant or plant part that is entirely homozygous 2n.

Hybrid female parent means a hybrid plant used as the plant that receives pollen in a cross.

Zucchini means plants of the genus *Cucurbita*. Zucchini are in fact a set of cultivars of the species *Cucurbita pepo* and of the subspecies *Cucurbita pepo* ssp. *pepo*.

Dose means the dose of radiation absorbed by the target, namely notably the reproductive plant material from the male parent.

Molecular marker means a specific fragment of a DNA sequence that can be identified within the genome of an individual and that can notably be used for localizing a gene of interest, verifying if an individual has inherited a particular characteristic from a parent or differentiating two individuals. It may or may not be a coding sequence. The marker can be dominant, codominant. Detection of the molecular marker, or its nondetection, makes it possible to select the individuals having the gene of interest or the particular characteristic, or, on the contrary, not select the individuals that do not have the gene of interest or the particular characteristic. In the present invention, the molecular markers permit the rapid testing of plants or plantlets during development and retain those that possess the required characteristics. Molecular markers of various kinds are known by a person skilled in the art: AFLP (amplification fragment length polymorphisms), SCAR (sequence characterized amplified region), SSR (microsatellites, simple sequence repeats), RFLP (restriction fragment length polymorphisms), etc.

Microsatellite marker or microsatellite sequence or SSR means a DNA sequence formed by a continuous repetition of motifs composed of 1 to 4 nucleotides. These microsatellite sequences are present on the entire genome, most often at the level of the introns of genes but also at the level of exons. The polymorphism of the microsatellites can be used as a genetic marker in order to identify an individual or a population, for example of plants.

During the creation and selection of plant varieties, stable and homogeneous transmission of the selected characters is an essential precondition. Also, being able to reliably ascertain the genotype and phenotype of the plants produced is fundamental. For maintaining a hybrid, preferably an F1 hybrid, stable parent lines are required. To obtain fixed plants, the plants are generally self-fertilized repeatedly, and the plants that do not have the required characteristics are eliminated at each generation. New techniques have permitted the development of plants from single gametes (n). Thus, androgenesis and gynogenesis have been developed. The use of gynogenesis with irradiated pollen is known for generating plants. However, as presented above, this technique has certain limits and principally the cases of pseudofertilization by the pollen, even when the latter has been fragmented by radiation, preferably X-rays or gamma rays. In fact, it may be that the pollen is not sufficiently degraded and that a DNA fragment of the irradiated pollen "pseudofertilizes" the female gametophyte whereas in this technique it should simply induce the development of a haploid embryo without modifying its genome. This embryo, and consequently the plant derived from this embryo, ideally should therefore not contain genome from the male parent that served for pollination of the reproductive material from the female parent. However, it is found that the progeny produced by gynogenesis induced by irradiated pollen can be of various kinds, notably:

haploid plants (with n chromosomes),
dihaploid plants (with 2n identical chromosomes n+n),
chimeras containing n chromosomes from the female parent and fragmented pieces of DNA from the male parent, whether or not recombined with the DNA from the female parent, either of haploid form, or having varied ploidy, or being dihaploid, having undergone a spontaneous doubling of their chromosome stock,
diploid plants resulting from fertilization
diploid plants having the same genome as the female parent plant (2n).

In the processes for creation of varieties, it is necessary that only the haploid plants H are conserved (including the haploid chimeras), which can then give, by doubling of the chromosome stock, the doubled haploids DH, and the dihaploid plants DiH to be certain of their homozygosity.

After extensive research, the inventors perfected this sorting, proposing a carefully selected range of doses of irradiation of the male gametophytes, which makes it possible to direct the gynogenesis toward a population of desired individuals (H, DiH) that is free or almost free of unwanted individuals.

Associating or substituting the choice of this range of doses with a selection process using molecular markers and/or flow cytometry goes in the same direction.

According to a preferred embodiment of the invention, the method involving induced gynogenesis with irradiation of pollen comprises the following successive stages:
a) Using the reproductive material from the male parent, preferably a flower,
b) Irradiating said reproductive plant material from the male parent at a dose between 160 and 190 Gamma Ray, preferably between 165 and 185 Gamma Ray (Gy) and quite particularly between 170 and 180 Gy,
c) Pollinating the reproductive plant material from the female parent with said irradiated reproductive plant material of the male parent,
d) Harvesting the fruits, the seeds of which carry the embryos,
e) Extracting the seeds from said fruits,
f) Extracting the embryos from said seeds,
g) Culturing the embryos on a suitable medium until a plant, preferably a plantlet, is obtained.

The stage of irradiation of the male reproductive material can be repeated several times, preferably two or three times, so that the genetic material is properly degraded. The quite particularly preferred irradiation dose of the male reproductive material is around 175 Gy.

In a quite particularly preferred embodiment of the invention, the method further comprises, after stage g) described above, a stage h) consisting of selecting the haploid plants H and/or DiH by flow cytometry, or by using molecular marker(s), or by flow cytometry and the use of molecular marker(s).

This stage h) of selection of the haploid plants H and/or DiH comprises:
—I— the use of specific molecular marker(s) of given allele(s) contained in the genetic material from the irradiated male parent for selecting, from the plants obtained at the end of stage g), the plants that are free from genetic material from the irradiated male parent or that possess an insufficient amount thereof to cause, in the progeny of said plants, a disjunction of one or more phenotypic and/or genotypic characters;
—II— the use of specific molecular marker(s) of given allele(s) contained in the genetic material from the hybrid female parent, said marker(s) making it possible to determine the homozygous/heterozygous state of the plants to be selected, i.e. the plants obtained at the end of stage g), said marker(s) being used for selecting the homozygous and essentially homozygous plants, in particular the DiH plants.

It is quite clear that during stage h) of selection, the order of using the given specific molecular markers contained in the genetic material from the male parent and of those contained in the genetic material from the female parent is unimportant. I and II are not necessarily performed in a precise order and can be concomitant (I and II at the same time) or successive (I then II, or II then I). Moreover, the selection stage h) can be repeated several times. This can be useful when using several specific molecular markers, for carrying out successive selections that are finer and finer with fewer and fewer individuals to be tested. Finally, when stage h) consists of selecting haploid plants H and/or DiH by flow cytometry and using molecular marker(s), flow cytometry can precede the use of molecular marker(s), the use of molecular marker(s) can precede flow cytometry, and the use of molecular marker(s) can be concomitant with flow cytometry.

Preferably, the parent plants are selected from the genus *Cucurbita*, Cucurbitaceae family, preferably from the species *Cucurbita pepo*, and, even more preferably, from the subspecies *Cucurbita pepo* ssp. *pepo*.

According to a remarkable characteristic of the invention, hybrid plants and F1 hybrid plants are used as the female plant. In fact, during production of the gametes of a hybrid plant or of an F1 hybrid plant, the chromosome pairings of the homologous chromosomes during the first division permit genetic recombinations and therefore give a great genetic variability of the gametes produced. The haploid plants H (giving the doubled haploids DH) and the dihaploid plants DiH resulting from these gametes and obtained by the method according to the present invention are genetically different from one another, thus providing the plant breeder with increased choice.

Stage a)

As a brief reminder of the life cycle of flowering plants, such as zucchini, a pollinated or self-pollinated flower will produce fruits which themselves contain seeds, which contain embryos, which will develop into plantlets and finally plants.

The male and female plant material is selected according to the required characteristics.

The male reproductive plant material that is collected and used mainly comprises flowers of a selected male plant but it can also be stamens or gametophytes or directly male gametes or pollen grains.

The flowers for example are advantageously harvested from the male parent plant at the moment of anthesis. One or two male flowers generally being used for fertilization of each female flower. For the preferred plants according to the invention, namely those of the genus *Cucurbita*, the male plants used according to the invention can be for example those whose genotypes are in the group comprising: JIB, JEDIDA, ESKENDARENI.

These male plants are particularly interesting as they are good pollinators, i.e. they emit large amounts of pollen.

The moment of harvesting the reproductive plant material from the male parent, preferably flowers, may be important. This moment is selected in relation to the development of the plant from which the flowers are obtained, the season etc. Thus, it is preferable to collect them at the time of anthesis and to fertilize the female flowers before they open.

Stage b)

The stage of irradiation b) of the reproductive plant material from the male parent, i.e. male gametophytes, such as pollen, is important for the success of the method for producing plants H (giving doubled haploids DH) and/or plants DiH.

The rays used are preferably gamma rays, but X-rays can also be used.

Irradiation is performed using suitable known means, such as gamma rays for example for a sufficient length of time for the reproductive plant material from the male parent to receive the prescribed dose on closed jars preferably containing ten to twelve male flowers per jar. For example, for JIB, the irradiation time is preferably between 20 minutes and an hour and a half.

The selected irradiation conditions (all parameters together) can give very satisfactory results, namely after pollination with the male reproductive plant material, sufficient production of fruits, which contain a sufficient number of embryos, which lead to plants, most of which possess the required characteristics. In fact, the majority of the embryos and therefore of the plants produced by the method according to the invention are H and/or DiH, the haploids giving doubled haploids.

Stage c)

Before carrying out stage c) of the method according to the invention, it may be advantageous to let some irradiated pollen grains germinate in a suitable medium, for example in a medium called MP15 (solution with 15% sucrose, 100 mg/L $H_3BO_3$ and 700 mg/L $CaCl_2, 2H_2O$), in order to verify that the irradiated pollen is still capable of germinating. After a given germination time, for example from 15 to 60 min, the pollen grains are then examined with a magnifying glass in order to estimate the percentages of germinated grains and of grains that have burst.

The reproductive material from the female parent used will have a genotype selected according to the plant to be created.

For the plants that are preferred according to the invention, namely those of the genus *Cucurbita*, the female plants used according to the invention can be for example those whose genotypes are in the group of genotypes comprising VN001, VG06, VN002, Odessa, VG 14, Tosca and VE 547 can also be used.

Stage c) of the method according to the invention consists essentially of pollinating the reproductive material from the female parent with the reproductive material from the male parent.

In this technique of gynogenesis, whole plants can be regenerated from the female gametophytes (ovaries or ovules) contained in the reproductive plant material from the female parent.

Pollination consists advantageously of bringing the male gametes and the female gametes in contact, but since the male gametes have been irradiated, there cannot be true fertilization of the female gametes but just elongation of the pollen tube and, by induction of the oosphere, development of an embryo.

Pollination of the reproductive plant material from the female parent can be done in various ways. The preferred techniques will be pollination by the "flower to flower" technique, where the whole surface of the stigmas (end of the pistils) is covered with the reproductive material from the male parent, but also pollination by brush. In the "flower to flower" technique, a flower or the reproductive material from the female parent is "fertilized" by a flower or the reproductive material from the male parent.

In the "brush" technique, a brush is used for transporting pollen grains from the reproductive material from the male parent to one or more flowers or reproductive material from the female parent.

Stage d)

Advantageously, in the days following pollination, good formation of the fruit (setting) is observed and flowers not forming fruit are removed. After pollination, the length of time after which the fruits are harvested depends on the family, genus and species in question.

Preferably, fruits that are of suitable maturity for extraction of the embryos are harvested.

The right time for collecting the fruit can be assessed on the basis of the morphology of the fruit and its general appearance.

For example, about 4 to 5 weeks after pollination (the length of time varies according to the genus and species), the fruits are collected and then preferably washed with water, optionally with a detergent (e.g. domestic hard soap), rinsed, dried and optionally cleaned again with alcohol.

Stage e)

The fruits are then opened to extract the seeds, preferably in sterile conditions, for example under laminar flow.

Stage f)

The seeds are then opened to extract the embryos from them.

Stage g)

The extracted embryos are cultured on a suitable medium, such as those described in the following examples, the S2P medium being preferred (cf. Table 8).

The embryos, for example, are cultivated in darkness, for one to two nights, at 20-25° C., then they are placed in full light for about 10 hours to 20 hours, e.g. for about 16 hours at the same temperature.

The embryos can be collected at various stages of embryonic development and certain stages may influence the yield of the method according to the invention. Thus, the embryos can be collected at the globular, heart, torpedo or cotyledon embryonic stage.

The embryos can be transplanted regularly, preferably about every 15 days, on the same medium or on a different culture medium appropriate to their stage of development, in particular once young leaves and rootlets appear.

When the plantlets are well developed, they are advantageously transplanted onto another suitable culture medium, e.g. with the composition given in the following examples (cf. Tables 8 and 9).

Stage h)

In a preferred variant of the method according to the invention, a stage of selection of the haploid plants H and/or DiH produced according to method is performed:

h1) by flow cytometry, and/or h2) by the use of a molecular marker.

This selection h1 and/or h2 is advantageously performed when the plant resulting from gynogenesis has a few leaves, a sample from the plant, preferably a leaf sample, being taken and analyzed following this selection stage h) of the method.

These selections h1) and/or h2), which can be applied, at the same time or at different times, in any order, or even intermittently, notably make it possible to determine the level of ploidy of the plants produced. Using these techniques, it is possible to discriminate between plants having 2n chromosomes and plants with n chromosomes. Thus, the plants having n chromosomes (haploid H) are stored and are later submitted to a stage of doubling of their chromosome stock, preferably with colchicine, thus producing doubled haploids (DH). The haploid plants H are sterile, whereas the doubled haploid plants DH and dihaploid DiH are not, and are particularly interesting for plant breeders.

In the case of selection h1) by flow cytometry, flow cytometry allows a reliable distinction to be made between plants 2n and plants n but it is not possible using this technique to differentiate dihaploid plants DiH (2n identical, homozygous) and heterozygous diploid plants 2n resulting from a defect of gametic reduction or from fertilization by the pollen grain. During this selection, the plants 2n as well as the plants n will be kept.

The plants 2n will be analyzed subsequently with molecular markers (stage h2 below) for finer selection between homozygous or essentially homozygous dihaploid plants 2n and heterozygous diploid plants 2n.

The haploid plants n (chimeric or nonchimeric) will be kept, with a view to being analyzed also by means of molecular markers and then with a view to obtaining homozygous or essentially homozygous doubled haploids after doubling of the chromosome stock.

Selection by flow cytometry allows the plants to be classified in two groups: haploid n and diploid 2n.

As methods that are alternative or complementary to flow cytometry, we may mention root tip chromosome counting or counting the number of chloroplasts in the guard cells of the stomata using a light microscope.

For its part, selection h2) by the use of a molecular marker offers the possibility of discrimination between the different types of plants 2n described above. This gives a considerable saving of time, space and cost. Moreover, this method of selection also offers greater fineness of analysis since it is also able to determine whether the haploid plants H or dihaploid DiH contain or do not contain the genome from the male parent, quickly and reliably. Thus, the method of selection by the use of a molecular marker makes it possible to determine the state of homozygosity of the plant in question, as well as its level of ploidy.

Selection h2) by the use of a molecular marker is preferably a stage h2) of selection of plants H and/or DiH comprising:

—I— the use of a specific molecular marker of given allele(s) contained in the genetic material from the irradiated male parent to select, from the plants obtained at the end of stage g), the plants that are free from genetic material from the irradiated male parent or that possess an insufficient amount thereof to cause, in the progeny of said selected plants, a disjunction of a phenotypic and/or genotypic character;

—II— the use of a specific molecular marker of given allele(s) contained in the genetic material from the hybrid female parent, said marker(s) making it possible to determine the homozygous/heterozygous state, optionally the level of ploidy, of the plants to be selected, i.e. the plants obtained at the end of stage g), said marker(s) being used for selecting the homozygous or essentially homozygous plants, in particular the plants DiH, it being stipulated that at least one marker used for each analysis can be a single marker, during a single analysis, notably within the scope of a codominant marker permitting immediate discrimination between several allelic forms of one and the same genetic marker. Preferably, a specific molecular marker of at least two alleles is used.

This specific molecular marker of allele(s) of the genetic material from the irradiated male parent and/or of one, preferably two, given alleles contained in the genetic material from the hybrid female parent is preferably a microsatellite marker SSR.

These various markers therefore serve, on the one hand, for identifying the plants that have a portion of male genetic material in their genome and, on the other hand, for differentiating homozygous plants from heterozygous plants. The more we use molecular markers, the more the level of homozygosity is defined. It is possible that at a given locus, the plant appears homozygous with the molecular markers used, but that it is not homozygous (or essentially homozygous) on all of its genes. It is therefore preferable to use several molecular markers (preferably at least 3, particularly 5 and more particularly 6) for reliable selection of the DiH plants. Said markers are selected in relation to the genomes of the parents used in gynogenesis. These molecular markers make it possible to differentiate between the homozygous haploid H and/or dihaploid DiH plants that are derived from female gametes and the heterozygous diploid plants (2n) resulting from non-gametic reduction, resulting from fertilization, or recombined resulting from partial fertilization with irradiated pollen.

The markers are advantageously selected so as to identify different alleles between the female plants giving the female gametes and the male plants giving the pollen that is irradiated. Thus, a plant resulting from partial fertilization possesses the alleles from the two parent plants (male and female) whereas a haploid H or dihaploid DiH plant only has the alleles from the female mother plant. The plants resulting from gynogenesis induced by the irradiated pollen and having alleles from the male parent in their genome, thus providing evidence of "fertilization", are therefore discarded. The haploid chimeras are a special case, as they have alleles from the female plant and from the male plant, but each allele is only present in a single copy.

To simplify, if the female plant bears the alleles A and B and the male plant bears the alleles C, all the regenerated plants bearing an allele C are considered to result from fertilization and are therefore discarded. Only the plants having only the allele A or the plants having only the allele B are retained. The plants having the allele A can be plants AA when they are dihaploid and A when they are haploid, the plants having the allele B can be plants BB when they are dihaploid and B when they are haploid. In the special case of haploid chimeras, their identification will be made possible by using several markers.

This or these molecular marker(s) can also serve for sorting and discarding the diploid plants derived from nonreduced gametes that are identical to the mother plant, as they are heterozygous for given, defined alleles of the female material used (mother plant). In this case, the molecular marker(s) is/are selected so as to identify alleles that are in the heterozygous state in female plants and therefore also in the plants derived from nonreduced gametes but which are either in the homozygous state for dihaploid plants, or as a single copy in haploid plants.

To simplify, if the female plant bears the alleles A and B, all the regenerated plants bearing the combination of alleles AB are considered to be derived from a nonreduced gamete. Once again, only the plants having only the allele A or the plants having only the allele B are retained.

The Markers:

According to a preferred embodiment of the invention, microsatellite markers or SSR are used for determining, in the plants obtained and tested, both the presence of the genome of the male parent and the homozygous/heterozygous state. They can also be used for determining the level of ploidy of the plants obtained and tested.

According to a particular and remarkable embodiment of the invention, the molecular marker(s) used, for application of the method according to the invention, is/are a microsatellite marker or microsatellite markers. Each of these microsatellite molecular markers is defined by a given nucleotide sequence of a given size, amplified by PCR using a pair of specific primers (a sense primer and an antisense primer). For a selection stage h), the molecular marker(s) that can be used in the present invention are the following eight markers CMAGN73, CMBR153, CMBR22, CMMP73, CUCNITRA, FAD2, PATL1, TJ3. Each of these markers is defined by a pair of nucleotide primers of given sequences (cf. below SEQ ID No. 1 to 16). It is quite clear that for this stage h), it is conceivable to use molecular markers (whether or not microsatellites) other than these eight markers mentioned above. The markers defined by the primer pairs SEQ ID No. 3 and SEQ ID No. 4; SEQ ID No. 5 and SEQ ID No. 6; SEQ ID No. 7 and SEQ ID No. 8; SEQ ID No. 9 and SEQ ID No. 10; SEQ ID No. 11 and SEQ ID No. 12 and/or SEQ ID No. 13 and SEQ ID No. 14 will preferably be used.

The sequences SEQ ID No. 1 to 16 are particularly interesting for application of the method according to the invention. Thus, the invention also relates to a molecular marker that can be used in the method according to the invention, of the microsatellite type (SSR), and advantageously selected from the group of microsatellite markers defined by the pairs of primers with the appended nucleotide sequences SEQ ID No. 1 to 16.

The invention preferably relates to a molecular marker that can be used in the method according to the invention, of the microsatellite type, and advantageously selected from the group comprising microsatellites defined by the pairs of primers with the appended nucleotide sequences SEQ ID No. 3 to 14.

To increase the reliability of selection, it is preferable to use a combination of two molecular markers according to the invention, namely preferably the microsatellite markers. Even more preferably according to the invention, a combination of three molecular microsatellite markers is used, particularly of four molecular microsatellite markers, and quite particularly a combination of five microsatellite markers is selected. Of course, it is possible to use more than five molecular markers if required. For these combinations of microsatellite markers used, the sequences of the primer pairs defining the marker(s) are selected from the sequences SEQ ID No. 1 to 16, preferably SEQ ID No. 3 to 14.

The microsatellite markers of sequences SEQ ID No. 1 to that can be used are notably specific to the Cucurbitaceae family, preferably of the genus *Cucurbita* and more preferably of the species *Cucurbita pepo*.

The microsatellite molecular marker(s) (SSR) of the zucchini according to the invention is/are selected in relation to the genotypes of plants for gynogenesis induced by irradiated pollen.

This/these microsatellite molecular marker(s) is/are defined by its/their nucleotide sequence, which will be detected by amplification by polymerase chain reaction (PCR) using specific primers whose sequences SEQ ID 1 to 16 are shown below in the examples. These primers can be fragments of cloned polynucleotides or of chemically synthesized oligonucleotides. The markers of sequences SEQ ID No. 3 to 14 will preferably be used.

Stage i) Chromosome Doubling

The plants selected and/or obtained at the end of stage h are haploid H, and dihaploid DiH plants. The plants H give dihaploid plants DiH when the doubling of the chromosome stock is spontaneous or doubled haploid DH when the doubling of the chromosome stock is effected by chemical or physical treatment, preferably by means of colchicine.

The method according to the invention therefore preferably comprises a stage i) of doubling of the chromosome stock of the haploid plants H, the stage of doubling of the chromosome stock preferably being performed by means of colchicine.

The plants DH that are already 2n are put out in soil in a greenhouse whereas the haploid plants H are preferably "colchicined" in vitro and then transplanted onto a suitable medium, then rooted and put out in soil in a greenhouse.

This technique of doubling of the chromosome stock by means of colchicine advantageously comprises the following successive stages:

1—Isolate the main growing tip of the plant as well as axillary buds if there are any.
2—Prepare a solution of colchicine and then sterilize it.
3—Put the cuttings in small sterile Petri dishes.
4—Pour in a sufficient amount of colchicine to cover them, then close the Petri dishes.
5—Leave to soak for several hours.
6—Take out the cuttings and rinse them in pots of sterile water.
7—After drying them a little on sterile paper, transplant all the cuttings onto their original medium.
8—Transplant developing buds on the original medium.
9—When the cuttings have rooted, bring them out in vivo on a substrate comprising a nutrient solution.

As explained previously, the present invention extends beyond the production of H, DH and DiH plants, by gynogenesis induced by irradiated pollen. In fact it proposes a novel method of optimization of said production of plants. This method makes it possible to overcome the problem of multifactorial variability and to generalize gynogenesis with irradiation of pollen for numerous plant species.

This method is based on a prior stage of determination of the suitable irradiation dose or doses for increasing the yields in the production of the plants, taking into account multiple factors such as the plant species, the genotypes of the male parent and of the female parent, the climatic and physiological conditions, the time of harvesting of the fruits, and the level of growth of the embryos collected with a view to culture thereof.

This prior stage consists essentially of employing, for each irradiation dose tested, a stage h') of selection of the H and/or DiH plants, h') being similar to h) as defined above, for then establishing the corresponding yields of plants and finally determining the dose or doses offering the best yields.

In addition to the yields of plants, in this prior stage it is also possible to obtain other results such as: the percentage of fruits obtained, the percentage of seeds obtained, the percentage of embryos and of H, DH and DiH plants, for a given irradiation dose.

Thus, the present invention relates to a method for producing haploid H, doubled haploid DH and/or dihaploid DiH plants, DH and DiH being homozygous or essentially homozygous, by gynogenesis with irradiation of the reproductive material from the male parent, characterized in that it comprises a prior stage of determination of the suitable irradiation dose or doses for increasing the yields of said plants as a function of multiple given factors, preferably selected from the plant species, the genotypes of the male parent and of the female parent, the climatic and physiological conditions, the time of harvesting of the fruits, the level of growth of the embryos collected with a view to culture thereof; the level of development of the embryos placed in culture, this prior stage comprising:
  i) testing, for a given factor, different irradiation doses on the reproductive plant material from the male parent,
  ii) employing, for each irradiation dose tested, a stage h') of selection of H and/or DiH plants, said stage h' comprising:
    —I— the use of a specific molecular marker of allele(s) of the genetic material from the irradiated male parent for selecting, from the plants obtained after gynogenesis induced by irradiated pollen, the plants that are free from plant material from the irradiated male parent or that possess an insufficient amount thereof to cause, in the progeny of said plants, a disjunction of a phenotypic and/or genotypic character;
    —II— the use of a specific molecular marker of an allele, preferably two specific given alleles of the genetic material from the hybrid female parent employed in gynogenesis, said marker making it possible to determine the homozygous/heterozygous state, optionally the level of ploidy, of the plants to be selected, i.e. of the plants obtained as a result of gynogenesis, said marker being used for selecting homozygous or essentially homozygous plants, in particular DiH plants;
  iii) counting, for each irradiation dose tested, the haploid plants H, or DiH, or H and DiH obtained;
  iv) calculating, for each irradiation dose tested and from the counts obtained in (iii), the yield of haploid plants H, or DiH, or H and DiH obtained;
  v) comparing the counts obtained in (iii) and/or the yields found in (iv) for deducing the suitable irradiation dose or doses.

As mentioned previously, stage h' comprises the use of markers and the order of using the specific molecular marker(s) of allele(s) of the male genetic material and that or those specific of allele(s) of the female material is unimportant. I and II are not necessarily carried out in a specified order and can be concomitant (I and II together) or successive (I then II, or II then I).

The invention also relates to the H and DiH plants themselves produced by the method as defined above, knowing that here the term "plant" encompasses all its stages of development: embryos, plantlet, adult plant. In particular, this applies to the haploid H and dihaploid DiH embryos obtained, as intermediates, by the method according to the invention as defined above and the plants regenerated from said embryos.

The invention also relates to the DH plants and plantlets obtained by the method as defined above with stage i) of colchicination.

Moreover, the invention also relates to the progeny as well as the seeds from the plants obtained by the method as defined above. In fact, the present application also relates to the progeny of the plants obtained by the method as defined above, said progeny being obtained by crossing said plants (DH or DiH) with one another or by crossing between a DH or DiH plant obtained by the method as defined above and a plant derived from a line or derived from repeated self-fertilizations.

Finally, the invention also relates to the seeds of plants obtained by the method as defined previously or from the embryos as defined above, as well as from plants derived from the progeny as defined above.

The preferred conditions of application of the methods described above also apply to the other objects of the above invention, notably to the method of optimization of production of plants by determination of the suitable irradiation dose, to the embryos and to the progeny of the plants obtained by the methods as well as their implementation.

The following examples illustrate the present application.

EXAMPLES

—I— The Method of Manufacture of Haploid H and/or Dihaploid DiH Plants by Gynogenesis Induced by Irradiated Pollen According to the Invention The experiments are carried out in a greenhouse whose temperature is 15° C. at night and 25° C. during the day.

The plants are grown in a bag of compost (2 plants per bag for the females and 3 plants per bag for the males), trained, and with drip irrigation.

The greenhouse is shaded and ventilated, and there is pest control by integrated biological protection.

The biological plant material used is constituted as follows:
Female plants: 2 genotypes
VN001: 66 plants
VG06: 66 plants
Male plants: 1 genotype
JIB: 90 plants The plants are labeled with a number and the name of their genotype.

Stage a)

The day before irradiation (or ionization), all the male and female plants are checked and only the flowers that will serve for pollination are kept. The number of male flowers at the right stage (the tip of the corolla begins to turn yellow) is counted to get an estimate of the number of pollinations that will be effected for each irradiation dose. The same is done for the female flowers at the right stage (the tip of the corolla begins to turn yellow).

Controls are prepared:
  Traveling control (V): the flowers travel in the same conditions but are not irradiated.
  Uncut, non-traveling control (NV): the flowers are picked just before pollination.

Stage b)

The male flowers are taken very early in the morning (5 h 30 to 6 h).

Packaging of the Flowers During Transport and Irradiation 10-12 flowers are put in each jar, which will be closed. The closed jars are placed in a cool box containing a cooling block. The treatment or the type of control is written on each jar. The reproductive material from the male parent is irradiated in the morning for one hour. This will be repeated on five different dates and two doses of irradiation will be tested

| | |
|---|---|
| dose H | 175 Gamma Ray (Gy) |
| dose O | 200 Gamma Ray (Gy) |

Estimation of the Germinating Capacity of the Irradiated Pollen

The pollen is germinated in a 45 µL drop of medium at 15% sucrose, 100 mg/L of $H_3BO_3$ and 700 mg/L of $CaCl_2$, $2H_2O$.

The drops are deposited on an EPDXY slide and left for 45 min in a Petri dish with water-saturated atmosphere, at 26° C.

The percentage of germinated grains and of burst grains is estimated using a magnifying glass.

Stage c)

Two hours after irradiation, the reproductive material from the male parent is used for pollination.

A female flower or reproductive material from the female parent is fertilized by a male flower or reproductive material from the male parent.

During the days following pollination, the setting of the fruits is checked, and if this is not happening, the fruit is removed.

Stage d)

The fruits will be harvested 4 to 5 weeks after pollination and labeled according to their genotype, the treatment of the male flowers or the type of control.

The fruits are preferably harvested in the morning.

Stage e)

Each fruit is washed with water and domestic hard soap, then it is rinsed and dried.

Under laminar flow, 70° alcohol is poured onto the fruit, then all of its surface is cleaned with sterile paper.

Starting from this stage, all the operations are to take place in sterile conditions, under laminar flow.

An incision is made all round the fruit, then the flesh is removed with a knife.

The seeds are recovered using a spoon, released from the flesh with tweezers and a scalpel, and then counted.

The seeds are stirred overnight.

Stage f)

Under laminar flow, the round jar is emptied into a sterile tall jar through a sterile funnel and then rinsed with sterile water. The seeds are opened one at a time under a binocular magnifying glass using tweezers and a scalpel.

The instruments are sterilized regularly to prevent any risk of contamination.

The embryo is deposited on S1C culture medium, the composition of which is shown in Tables 8 and 9 given below, in 60×15 Petri dishes, 4 embryos per Petri dish.

The embryos obtained after fertilization by irradiated pollen do not have the same shape as normal embryos.

The Petri dishes are placed in darkness for 1 to 2 nights in a room at 20/25° C., then they are put in the light in the same room at 20/25° C. for 16 h.

Stage g)

The embryos are cultured on the culture medium by the PPM (plant preservative mixture) marketed by the company Kalys®.

The embryos are transplanted on S3P medium (P=PPM), the composition of which is shown in Tables 8 and 9.

The Petri dishes are inspected regularly. The embryos are transplanted if there is contamination by a bacterium or a fungus.

The embryos are transplanted every 15 days to a Petri dish on fresh medium until they are sufficiently developed.

Once young leaves and rootlets appear, the embryos are transferred onto medium in S3P tubes (cf. composition in Tables 8 and 9).

The well-developed plantlets are then transplanted to a jar on S2P or S4P, the compositions of which are shown in Tables 8 and 9.

Stage h)

Once foliar development is sufficient, a sample is taken from each plant and is analyzed by flow cytometry and using molecular markers SSR.

Stage h1)

A sample is taken from each plant and the level of ploidy is analyzed by flow cytometry according to the protocols developed by Laat et al. in Theo. Appl. Genet, 1984, 67: 463-467 and in Plant Breeding, 1987, 99: 303-307. The plants with abnormal, indeterminate ploidy are discarded and the plants with n chromosomes are distinguished from the plants with 2n chromosomes.

Stage h2)

A sample is taken from each plant, and the DNA is extracted according to the CTAB protocol modified by Tomas et al. (1989). The SSR marker(s) is/are selected from the SSRs defined by the primer pairs of sequences SEQ ID No. 1 to SEQ ID No. 16 below. The marker FAD2 is defined by the primer pairs SEQ ID No. 11 and SEQ ID No. 12. The PCR reaction is performed in a reaction volume of 5 µl constituted of half of 5 µl of diluted DNA, 0.85 µl of water, 1 µl of buffer 10×, 1 µl of $MgCl_2$ (25 mM), 1 µl of dNTP (2.5 mM), 0.5 µl of each primer (2 µM), 0.075 of M13 tail (8 µM) and 0.075 of Taq Invitrogen (5 U/µl).

The PCR reaction consists of several cycles of amplification, described as follows: 1 stage of 5 minutes at 94° C., 10 cycles at 94° C. for 15 seconds then degrees for 15 seconds and finally 72° C. for 30 seconds, then 30 cycles at 94° C. for 15 seconds then 52 degrees for 15 seconds and finally 72° C. for 30 seconds, with a final elongation performed at 72° C. for 7 minutes.

For carrying out the selection stage h (in particular h2), of the following eight preferred microsatellite molecular markers (SSR) defined by the following nucleotide primers SEQ ID No. 1 to 16, the markers FAD2, CMAGN73, CUCNITRA, TJ3, CMBR153 and PALT1 were used:

CMAGN73 marker defined by the primer pair with the following nucleotide sequences:

5' ATCCAACTCGACCAAGAAAC 3' (SEQ ID No. 1) as the sense primer
and
3' CAGCTCTACAACAACATCTC 5' (SEQ ID No. 2) as the antisense primer.

CMBR153 marker defined by the primer pair with the following nucleotide sequences:

5' TCAAAGACAAGAAGACCAACCA 3' (SEQ ID No. 3) as the sense primer
and
3' TGTGCTAAGAGAGAGAGAAGATTG 5' (SEQ ID No. 4) as the antisense primer.

CMBR22 marker defined by the primer pair with the following nucleotide sequences:
5' CCAAAACGACCAAATGTTCC 3' (SEQ ID No. 5) as the sense primer
and
3' ATACAGACACGCCTTCCACC 5' (SEQ ID No. 6) as the antisense primer.
CMMP73 marker defined by the primer pair with the following nucleotide sequences:
5' GCACTTTGAGTAAGAAGCAGA 3' (SEQ ID No. 7) as the sense primer
and
3' GCTGTGAGGTTGACTACGA 5' (SEQ ID No. 8) as the antisense primer.
CUCNITRA marker defined by the primer pair with the following nucleotide sequences:
5' CAAACCATAACTTCCAAGG 3' (SEQ ID No. 9) as the sense primer
and
3' GGAGATCGACGAATTTGA 5' (SEQ ID No. 10) as the antisense primer.
FAD2 marker defined by the primer pair with the following nucleotide sequences:
5' CACGAGCAGAGAGATAATAAA 3' (SEQ ID No. 11) as the sense primer
and
3' CCTGAAAGAGAGGAAGAAGAA 5' (SEQ ID No. 12) as the antisense primer.
PATL1 marker defined by the primer pair with the following nucleotide sequences:
5' TACTCCGCCCTCTCTCTC 3' (SEQ ID No. 13) as the sense primer
and
3' CAGGTGCAGAATCTGGTAGT 5' (SEQ ID No. 14) as the antisense primer.
TJ3 marker defined by the primer pair with the following nucleotide sequences:
5' TGGGCCTACGCTACAAACTT 3' (SEQ ID No. 15) as the sense primer
and
3' AGCAGCACAAAAGCACTTCA 5' (SEQ ID No. 16) as the antisense primer.

These primers were performed according to the methods known by a person skilled in the art. For given microsatellite markers, depending on the size of the fragments amplified by PCR with the specific primers (cf. Tables 3 to 6 below), it was possible to select the H, or DiH, or H and DiH plants. Thus, the molecular markers used make it possible, among other things, to determine whether a plant is or is not the result of fertilization, whether or not it is homozygous.

If the plant resulted from fertilization between the male plant material and the female plant material or if it has not undergone gametic reduction, it is eliminated after analysis with the molecular markers SSR but if it is a dihaploid plant, it is kept.

The plants n undergo treatment with colchicine in vitro for doubling their chromosome stock (cf. stage i) below). Then they are transplanted, rooted and taken out.

Stage i) Doubling of the chromosome stock (treatment with colchicine):

1—Isolate the main growing tip as well as the axillary buds if there are any (cuttings).
2—Prepare a solution of colchicine at 5 per 1000 (0.5 g of colchicine in 100 ml) and sterilize it.
3—Put the cuttings in small sterile Petri dishes (BP 35×10).
4—At a microbiological safety station, pour a sufficient amount of colchicine to cover the cuttings (6 to 8 ml) and then close the dish.
5—Leave to soak for 2 hours.
6—Take out the cuttings and rinse them in small pots of sterile water.
7—After drying them slightly on sterile paper, transplant all the cuttings into ball-shaped jars on their original medium.
8—Transplant developing buds onto the original medium, numbering them from C1 ("C" for colchicine) to CX.
9—When the cuttings have rooted and are therefore ready, bring them out in vivo on coco substrate with watering using a nutrient solution.

—II— Results of Setting and Numbers of Fruits in Relation to the Genotypes (Table 1)

TABLE 1

| Irradiation No. | | 1 | 2 | 3 | 4 | 5 | |
|---|---|---|---|---|---|---|---|
| Day and Time irradiation | | D-1 16 H | D 8 H | D-1 16 H | D 8 H | D 8 H | |
| Day and Time pollination | | D 7 H | D 11 H 30 | D 7 H | D 12 H 15 | D 11 H 30 | Total |
| VG06 general | Number of fruits VG06 pollinated | 10 | 9 | 19 | 11 | 12 | 61 |
| | Number of fruits VG06 at term | 10 | 9 | 19 | 11 | 12 | 61 |
| | % hooked of VG06 | 100% | 100% | 100% | 100% | 100% | 100% |
| VN001 general | Number of fruits VN001 pollinated | 11 | 10 | 19 | 15 | 9 | 61 |
| | Number of fruits VN001 at term | 11 | 10 | 16 | 14 | 8 | 59 |
| | % hooked of VN001 | 100% | 100% | 100% | 93% | 88% | 97% |
| VG06 detail (Number of fruits) | VG06 175 Gy JIB | 7 | 7 | 13 | 7 | 7 | 41 |
| | VG06 200 Gy JIB | 3 | 2 | 4 | 2 | 3 | 14 |
| | Controls | X | X | 2 | 2 | 2 | 6 |
| VN001 detail (Number of fruits) | VN001 175 Gy JIB | 7 | 7 | 12 | 9 | 6 | 41 |
| | VN001 200 Gy JIB | 3 | 2 | 4 | 5 | 2 | 16 |
| | Controls | 1 | 1 | X | X | X | 2 |
| Total | | 21 | 19 | 35 | 30 | 20 | 125 |

It can be seen that there is very good general setting. 127 fertilizations permitted development of 125 fruits, i.e. 98% success.

III—Results Obtained as a Function of the Genotypes of the Parents and of the Irradiation (Ionization) Dose Used (Table 2)

The 175 Gy and 200 Gy doses were tested on the reproductive plant material from the male parent JIB and the results of gynogenesis with the female plant material (VN001 and VG06) are shown below.

TABLE 2

| Genotype | Dose Gy | Number of fruits | Number of seeds | Number of embryos | Average size of embryos, cm | Number of plants in tubes |
|---|---|---|---|---|---|---|
| VG06 | 175 (H) | 44 | 9707 | 289 | 0.18 | 24 |
|  | 200 (O) | 16 | 3710 | 30 | 0.12 | 1 |
| VN001 | 175 (H) | 41 | 2435 | 62 | 0.13 | 4 |
|  | 200 (O) | 16 | 722 | 11 | 0.1 | 0 |

The table shows that the dose 200 Gy used for irradiation of the pollen is too strong to obtain, with the genotypes VG06 and VN001, embryos that develop.

Conversely, the dose of 175 Gy is more suitable as it makes it possible to produce not only more fruits with the two female genotypes tested (VG06 and VN001) but also more embryos that develop (24 for VG06 and 4 for VN001).

IV—Selection with Molecular Markers

1. Analysis of the Plants Derived from VN001

A/ Analysis of the Plants in Order to Identify the Plants Containing Genetic Material from the Male Parent (Table 3):

The VN001 hybrid plants used as the female in the method for producing plants by gynogenesis with irradiation of the reproductive material from the male parent possess an allele of 171 base pairs for the FAD2 marker whereas the JIB plants used as the male plant possess an allele of 169 base pairs for this same marker.

Similarly, the allele of the CMAGN73 marker is of 128 base pairs for VN001, whereas it is of 132 for JIB and the allele of the Cucnitra marker is of 160 base pairs for VN001, whereas it is of 165 for JIB.

Table 3 shows the molecular analysis of the plants obtained from VN001 according to the method of the present invention and indicates, for each plant tested, the presence or absence of genetic material from the male parent.

TABLE 3

| Plant No. | Markers | | |
|---|---|---|---|
|  | FAD2 | CMAGN73 | CUCNITRA |
| JIB | 169 |  | 132 | 165 |
| VN001 |  | 171 | 128 | 160 |
| Plant 1 | X |  | X | X |
| Plant 2 |  | X | X | X |
| Plant 3 | X |  | X |  |
| Plant 4 | X | X | X | X |

Table 3 shows that the markers FAD2, CMAGN73 and CUCNITRA make it possible to identify the plants possessing the male genome. After PCR using primers (SEQ ID No. 11 and 12 defined above) specific to the molecular marker FAD2, analysis of this PCR reveals, for plants 1, 3 and 4, the presence of the allele of 169 base pairs specific to the male reproductive material JIB. Plants 1, 3 and 4 therefore possess male genome in their genome. These results therefore demonstrate that the use of particular molecular marker(s) (here CMAGN73, CUCNITRA and particularly FAD2) makes it possible to carry out an effective and reliable analysis and selection of the origin of the plants produced.

B/ Analysis of the Plants in Order to Identify the Homozygous Plants of the Heterozygous Plants (Table 4):

The VN001 hybrid plants used as female in the method for producing plants by gynogenesis with irradiation of the reproductive material from the male parent possess an allele of 130 base pairs and an allele of 138 base pairs for marker TJ3.

Similarly, the alleles of the marker CMBR153 are of 166 and 182 base pairs for VN001, and those of PLAT1 are of 195 and 204 base pairs.

Table 4 shows the molecular analysis of the plants obtained from VN001 according to the method of the present invention and indicates, for each plant tested, the presence of one or more alleles of each marker.

TABLE 4

| Plant No. | Markers | | | | | |
|---|---|---|---|---|---|---|
|  | TJ3 | | CMBR153 | | PALT1 | |
| VN001 | 130 | 138 | 166 | 182 | 195 | 204 |
| Plant 1 | X | X | X |  | X |  |
| Plant 2 | X |  | X |  | X |  |
| Plant 3 | X | X | X |  | X |  |
| Plant 4 | X |  | X |  | X |  |

This table shows that plants 1 and 3 are heterozygous. In fact, owing to the marker TJ3, we find the presence of an allele of 130 base pairs and of another allele of 138 base pairs. With the markers TJ3, CMBR153 and PALT1, plants 2 and 4 appear homozygous. These results demonstrate that the use of particular molecular marker(s) (here TJ3, CMBR153, PATL1) makes it possible to carry out an effective and reliable analysis and selection of the homozygous/heterozygous state, and optionally of ploidy, of the plants produced.

2. Analysis of the Plants Obtained from VG06

A/ Analysis of Plants in Order to Identify Plants Containing Genetic Material from the Male Parent (Table 5):

The VG06 hybrid plants used as female in the method for producing plants by gynogenesis with irradiation of the reproductive material from the male parent possess an allele of 171 base pairs for the FAD2 marker whereas the plants JIB used as the male plant possess an allele of 169 base pairs for this same marker.

Similarly, the allele of the Cucnitra marker is of 160 for VN001, whereas it is of 165 for JIB and the allele of the CMAGN73 marker is of 128 base pairs for VG06, whereas it is of 132 for JIB.

Table 5 shows the molecular analysis of the plants obtained from VG06 according to the method of the present invention and indicates, for each plant tested, the presence or absence of genetic material from the male parent.

TABLE 5

| Plant No. | FAD2 (169) | FAD2 (171) | CUCNITRA (165) | CUCNITRA (160) | CMAGN73 (132) | CMAGN73 (128) |
|---|---|---|---|---|---|---|
| Jib | 169 | | 165 | | 132 | |
| VG06 | | 171 | | 160 | | 128 |
| Plant 1 | | X | X | | X | |
| Plant 2 | | | | | X | |
| Plant 3 | | | | | X | |
| Plant 4 | X | X | X | | X | X |
| Plant 5 | X | X | X | | X | |
| Plant 6 | X | X | X | | X | X |
| Plant 7 | | X | X | | X | |
| Plant 8 | | X | X | | X | |
| Plant 9 | | X | X | | X | X |
| Plant 10 | X | X | X | | X | X |
| Plant 11 | X | | X | X | X | |
| Plant 12 | X | X | X | X | X | X |
| Plant 13 | | X | X | | X | X |
| Plant 14 | | X | X | | | |
| Plant 15 | | X | | | X | |
| Plant 16 | | X | | | X | |
| Plant 17 | | X | | | X | |
| Plant 18 | X | X | | | X | |
| Plant 19 | X | | | | X | |

In the same way as for the analyses with VN001 (Table 3), owing to the molecular markers FAD2, CUCNITRA, CMAGN73, this table makes it possible to define the plants containing the male genome: plants 4, 5, 6, 9, 10, 11, 12, 13, 18 and 19. These results therefore demonstrate that the use of particular molecular marker(s) (here FAD2, CUCNITRA, CMAGN73) makes it possible to perform an effective and reliable analysis and selection of the origin of the plants produced.

B/ Analysis of the Plants in Order to Identify the Homozygous Plants of the Heterozygous Plants (Table 6):

The VG06 hybrid plants used as female in the method for producing plants by gynogenesis with irradiation of the reproductive material from the male parent possess an allele of 130 base pairs and an allele of 138 base pairs for the TJ3 marker.

Similarly, the alleles of the CMBR153 marker are of 166 and 182 base pairs for VG06, and those of PLAT1 are of 195 and 204 base pairs.

Table 6 shows the molecular analysis of the plants obtained from VG06 according to the method of the present invention and indicates, for each plant tested, the presence of one or more alleles of each marker.

TABLE 6

| Plant No. | TJ3 | | CMBR153 | | PALT1 | |
|---|---|---|---|---|---|---|
| | 130 | 138 | 166 | 182 | 195 | 204 |
| VG06 | 130 | 138 | 166 | 182 | 195 | 204 |
| Plant 1 | X | X | X | X | X | |
| Plant 2 | X | X | | | X | |
| Plant 3 | X | X | X | X | | X |
| Plant 4 | X | | X | | X | |
| Plant 5 | X | X | X | X | | X |
| Plant 6 | X | | | X | | X |
| Plant 7 | X | X | | | | X |
| Plant 8 | X | X | X | X | | X |
| Plant 9 | X | | X | X | X | X |
| Plant 10 | X | X | X | X | X | X |
| Plant 11 | X | | X | X | | X |
| Plant 12 | X | | X | X | | X |
| Plant 13 | X | X | X | X | X | X |
| Plant 14 | | | X | X | | X |
| Plant 15 | X | X | X | X | | X |
| Plant 16 | X | | X | X | | X |
| Plant 17 | X | X | X | X | | X |
| Plant 18 | X | | X | X | | X |
| Plant 19 | X | X | X | X | | X |

Table 6 shows that with the markers TJ3, CMBR153 and PALT1, only plants 4 and 6 are homozygous, the other plants appear heterozygous with these molecular markers. These results demonstrate that the use of particular molecular marker(s) (here TJ3, CMBR153, PATL1) makes it possible to perform an effective and reliable analysis and selection of the homozygous/heterozygous state, and optionally of ploidy, of the plants produced.

V—Synoptic Table of the Effect of the Irradiation Doses on the Production of Heterozygous Plants and of Haploid Plants (Table 7)

TABLE 7

| Irradiation doses | Year | Number of plants tested by flow cytometry and SSR | Number of heterozygous plants (2n) | Number of haploid plants (n) |
|---|---|---|---|---|
| 25 Gy/150 Gy | 2003 | 628 | 628 | 0 |
| 125 Gy/150 Gy | 2004 | 1734 | 1734 | 0 |
| 125 Gy | 2005 | 2931 | 2931 | 0 |
| 125 Gy/150 Gy | 2006 | 461 | 460 | 0 |
| 175 Gy/200 Gy | 2007 | 20 | 10 | 10 |

Doses from 25 to 50 Gy lead to the production of numerous plants, all identified as heterozygous. The dose of 175 Gy makes it possible not only to reduce the number of plants produced to be analyzed but also to increase considerably the number of haploid plants among the plants produced. As has been broadly explained above, these haploid plants are particularly interesting. Consequently, this table demonstrates that the irradiation dose has an influence on the success of the method employed in the present invention and that this dose can be optimized for better production of haploid plants. Thus, with the dose of 175 Gy, it is possible to improve the production of haploid plants H and doubled haploid plants DH, by gynogenesis induced by an irradiated male gametophyte and consequently obtain stabilization of the genome of the plants produced with a reduced number of generations.

VI—Culture Media

TABLE 8

| Composition | SIC | S3P | S2P | S4P |
|---|---|---|---|---|
| TZ2 | X | | ½ X | |
| TZ4 | | X | | ½ X |
| Sucrose | | 30 g/l | 5 g/l | 5 g/l |
| Plant Preservation Mixture (Kalys ®) | | 1 ml/l | 1 ml/l | 1 ml/l |
| Vitro Agar | 8 g/l | 8 g/l | 8 g/l | 8 g/l |
| pH | 5.9 | 5.9 | 5.9 | 5.9 |
| Autoclave 120° C./20 min | | | | |
| Kinetin | 0.05 mg/l | 0.05 mg/l | | |
| Naphthaleneacetic acid | 0.05 mg/l | 0.05 mg/l | | |
| Cefotaxime | 300 mg/l | | | |

TABLE 9

| Composition of media | TZ2 | TZ4 |
|---|---|---|
| Macro Murashige and Skoog | X | |
| Macro CP | | X |
| Micro Murashige and Skoog | X | |
| Micro CP | | X |
| MOREL Vitamins | X | |
| P Vitamins | | X |
| Sucrose | 3% | 10 |

Details of the Compositions in Table 9:

TZ4 Medium Without Sucrose or Agar:

| Macro element CP: in mg · L$^{-1}$ | |
|---|---|
| KNO$_3$ | 2150 |
| NH$_4$NO$_3$ | 1238 |
| Ca(NO$_3$)$_2$, 4 H$_2$O | 50 |
| CaCl$_2$, 2H$_2$O | 313 |
| MgSO$_4$, 7H$_2$O | 412 |
| KCl | 7 |
| Na H$_2$PO$_4$, H$_2$O | 38 |
| KH$_2$PO$_4$ | 142 |
| (NH$_4$)2SO$_4$ | 34 |
| Iron EDTA: in mg · L$^{-1}$ | |
| FeSO$_4$, 7H$_2$O | 27.8 |
| Na$_2$EDTA | 37.8 |
| Micro Element CP: in mg · L$^{-1}$ | |
| MnSO$_4$, H$_2$O | 22.13 |
| H$_3$BO$_3$ | 3.15 |
| ZnSO$_4$, 7H$_2$O | 3.62 |
| Na$_2$MoO$_4$ | 0.188 |
| CuSO$_4$, 5H$_2$O | 0.016 |
| CoCl$_2$ | 0.016 |
| KI | 0.695 |

| P vitamins: in µg · L$^{-1}$ | |
|---|---|
| Meso Inositol | 50.35 mg · L$^{-1}$ |
| Thiamine | 600 µg · L$^{-1}$ |
| Nicotinic acid | 700 |
| Pyridoxine | 5500 |
| Calcium panthothenate | 500 |
| Biotin | 5 |

TZ2 Medium with Sucrose:

| Macro element MS: in mg · L$^{-1}$ | |
|---|---|
| KNO$_3$ | 1900 |
| NH$_4$NO$_3$ | 1650 |
| CaCl$_2$ | 332.02 |
| MgSO$_4$ | 180.54 |
| KH$_2$PO$_4$ | 170 |
| FeNa EDTA: | 36.70 |
| Micro Element MS: in mg · L$^{-1}$ | |
| MnSO$_4$, H$_2$O | 16.90 |
| H$_3$BO$_3$ | 6.20 |
| ZnSO$_4$, 7H$_2$O | 8.60 |
| Na$_2$MoO$_4$, 2H$_2$O | 0.25 |
| CuSO$_4$, 5H$_2$O | 0.025 |
| CoCl$_2$, 6H$_2$O | 0.025 |
| KI | 0.83 |
| MOREL vitamins: in mg · L$^{-1}$ | |
| Meso Inositol | 100 mg · L$^{-1}$ |
| Thiamine | 1 |
| Nicotinic acid | 1 |
| Pyridoxine | 1 |
| Calcium panthothenate | 1 |
| Biotin | 0.01 |
| Sucrose: | 30 000.00 mg/l |

The invention claimed is:

1. A method for producing haploid (H), doubled haploid (DH) and/or dihaploid (DiH) plants, doubled haploid (DH) and dihaploid (DiH) plants being homozygous or essentially homozygous, said method being by gynogenesis induced by irradiated pollen, said method comprising:
   a stage of irradiation of the reproductive material from a male parent at a dose between about 165 and 185 Gamma Ray (Gy) and a stage of selection of haploid (H), or dihaploid (DiH), or haploid (H) and dihaploid (DiH) plants by the use of molecular marker(s),
   wherein the parent plants are selected from the species *Cucurbita pepo*.

2. The method as claimed in claim 1, comprising the following successive stages:
   a) Use reproductive material from a male parent;
   b) Irradiate said reproductive material from the male parent at a dose between 165 and 185 Gamma Ray;
   c) Pollinate the reproductive material from a hybrid female parent with said irradiated reproductive material from the male parent;
   d) Harvest the fruits whose seeds bear embryos;
   e) Extract the seeds from said fruits;
   f) Extract the embryos from said seeds;
   g) Place the embryos in culture on a suitable medium until a plant is obtained; and
   h) Selecting the haploid plants (H), or dihaploid plants (DiH), or haploid (H) and dihaploid (DiH) plants by the use of molecular marker(s).

3. The method as claimed in claim 2, wherein that stage h of selection of the haploid plants (H), or dihaploid plants (DiH), or haploid (H) and dihaploid (DiH) plants comprises:
   —I— the use of specific molecular marker(s) of given allele(s) contained in the genetic material from the male parent for selecting, from the plants obtained at the end of stage g), the plants that are free from genetic material from the male parent or that possess an insufficient amount thereof to cause, in the progeny of said plants, a disjunction of a phenotypic and/or genotypic character; and,
   —II— the use of specific molecular marker(s) of given allele(s) contained in the genetic material from the hybrid female parent, to determine the homozygous/heterozygous state of the plants to be selected, i.e. the plants obtained at the end of stage g), said marker(s) being used for selecting homozygous or essentially homozygous plants.

4. The method as claimed in claim 1 further comprising a stage i) of doubling of the chromosome stock of the haploid plants (H).

5. The method as claimed in claim 4, wherein that stage i) of doubling of the chromosome stock is performed by means of colchicine.

6. The method as claimed in claim 1, for producing haploid (H), doubled haploid (DH) and/or dihaploid (DiH) plants, doubled haploid (DH) and dihaploid (DiH) plants being homozygous or essentially homozygous, by gynogenesis induced with irradiation of the reproductive material from the male parent,
   comprising a prior stage of determination of the suitable irradiation dose or doses for increasing the yields of said plants as a function of multiple given factors, selected from the group consisting of the genotypes of the male parent and of the female parent; the climatic and physiological conditions; the time of harvesting of the fruits; the level of growth of the embryos collected with a view to culture thereof; and the level of development of the embryos placed in culture; said prior stage comprising:
   i) testing, for a given factor, different irradiation doses on the reproductive plant material from the male parent,
   ii) employing, for each irradiation dose tested, a stage h') of selection of haploid plants (H), or dihaploid plants (DiH), or haploid (H) and dihaploid (DiH) plants, said stage h') comprising:
      —I— the use of specific molecular marker(s) of allele(s) of the genetic material from the male parent for selecting, from the plants obtained as a result of gynogenesis induced by the irradiated pollen, the plants that are free from plant material from the male parent or which possess an insufficient amount thereof to cause, in the progeny of said plants, a disjunction of a phenotypic and/or genotypic character; and
      —II— the use of specific molecular marker(s) of given specific allele(s) of the genetic material of the hybrid female parent employed in gynogenesis, to determine the homozygous/heterozygous state of the plants to be selected, i.e. of the plants obtained as a result of gynogenesis, said marker(s) being used for selecting homozygous or essentially homozygous plants;

iii) counting, for each irradiation dose tested, haploid plants (H), or dihaploid plants (DiH), or haploid (H) and dihaploid (DiH) plants obtained;

iv) calculating, for each irradiation dose tested and from the counts obtained in (iii), the yield of haploid plants (H), or dihaploid plants (DiH), or haploid (H) and dihaploid (DiH) plants obtained; and v) comparing the counts obtained in (iii) and/or the yields found in (iv) for deducing the suitable irradiation dose or doses.

7. The method of claim 1, wherein the molecular marker(s) used is/are a microsatellite marker or microsatellite marker(s) (SSR).

8. The method of claim 1, wherein the molecular marker(s) used is/are selected from the markers defined by a primer pair or primer pairs of nucleotide sequences SEQ ID No. 1 to 16.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: sense primer of CMAGN73

<400> SEQUENCE: 1
atccaactcg accaagaaac                                                   20
```

-continued

```
<210> SEQ ID NO 2
<211> LENGTH: 20
<212> TYPE: DNA
<213> ORGANISM: Artificial Sequence
<220> FEATURE:
<223> OTHER INFORMATION: antisense primer of CMAGN73

<400> SEQUENCE: 2
cagctctaca acaacatctc                                                     20

<210> SEQ ID NO 3
<211> LENGTH: 22
<212> TYPE: DNA
<213> ORGANISM: Artificial Sequence
<220> FEATURE:
<223> OTHER INFORMATION: sense primer of CMBR153

<400> SEQUENCE: 3
tcaaagacaa gaagaccaac ca                                                  22

<210> SEQ ID NO 4
<211> LENGTH: 26
<212> TYPE: DNA
<213> ORGANISM: Artificial Sequence
<220> FEATURE:
<223> OTHER INFORMATION: antisense primer of CMBR153

<400> SEQUENCE: 4
tgtgctaaga gagagagaga agattg                                              26

<210> SEQ ID NO 5
<211> LENGTH: 20
<212> TYPE: DNA
<213> ORGANISM: Artificial Sequence
<220> FEATURE:
<223> OTHER INFORMATION: sense primer of CMBR22

<400> SEQUENCE: 5
ccaaaacgac caaatgttcc                                                     20

<210> SEQ ID NO 6
<211> LENGTH: 20
<212> TYPE: DNA
<213> ORGANISM: Artificial Sequence
<220> FEATURE:
<223> OTHER INFORMATION: antisense primer of CMBR22

<400> SEQUENCE: 6
atacagacac gccttccacc                                                     20

<210> SEQ ID NO 7
<211> LENGTH: 21
<212> TYPE: DNA
<213> ORGANISM: Artificial Sequence
<220> FEATURE:
<223> OTHER INFORMATION: sense primer of CMMP73

<400> SEQUENCE: 7
gcactttgag taagaagcag a                                                   21

<210> SEQ ID NO 8
<211> LENGTH: 19
<212> TYPE: DNA
<213> ORGANISM: Artificial Sequence
<220> FEATURE:
<223> OTHER INFORMATION: antisense primer of CMMP73
```

```
<400> SEQUENCE: 8
gctgtgaggt tgactacga                                                    19

<210> SEQ ID NO 9
<211> LENGTH: 19
<212> TYPE: DNA
<213> ORGANISM: Artificial Sequence
<220> FEATURE:
<223> OTHER INFORMATION: sense primer of CUCNITRA

<400> SEQUENCE: 9
caaaccataa cttccaagg                                                    19

<210> SEQ ID NO 10
<211> LENGTH: 18
<212> TYPE: DNA
<213> ORGANISM: Artificial Sequence
<220> FEATURE:
<223> OTHER INFORMATION: antisense primer of CUCNITRA

<400> SEQUENCE: 10
ggagatcgac gaatttga                                                     18

<210> SEQ ID NO 11
<211> LENGTH: 21
<212> TYPE: DNA
<213> ORGANISM: Artificial Sequence
<220> FEATURE:
<223> OTHER INFORMATION: sense primer of FAD2

<400> SEQUENCE: 11
cacgagcaga gagataataa a                                                 21

<210> SEQ ID NO 12
<211> LENGTH: 21
<212> TYPE: DNA
<213> ORGANISM: Artificial Sequence
<220> FEATURE:
<223> OTHER INFORMATION: anstisense primer of FAD2

<400> SEQUENCE: 12
cctgaaagag aggaagaaga a                                                 21

<210> SEQ ID NO 13
<211> LENGTH: 18
<212> TYPE: DNA
<213> ORGANISM: Artificial Sequence
<220> FEATURE:
<223> OTHER INFORMATION: sense primer of PATL1

<400> SEQUENCE: 13
tactccgccc tctctctc                                                     18

<210> SEQ ID NO 14
<211> LENGTH: 20
<212> TYPE: DNA
<213> ORGANISM: Artificial Sequence
<220> FEATURE:
<223> OTHER INFORMATION: antisense primer of PATL1

<400> SEQUENCE: 14
caggtgcaga atctggtagt                                                   20
```

```
<210> SEQ ID NO 15
<211> LENGTH: 20
<212> TYPE: DNA
<213> ORGANISM: Artificial Sequence
<220> FEATURE:
<223> OTHER INFORMATION: sense primer of TJ3

<400> SEQUENCE: 15
tgggcctacg ctacaaactt                                                    20

<210> SEQ ID NO 16
<211> LENGTH: 20
<212> TYPE: DNA
<213> ORGANISM: Artificial Sequence
<220> FEATURE:
<223> OTHER INFORMATION: antisense primer of TJ3

<400> SEQUENCE: 16
agcagcacaa aagcacttca                                                    20
```